(12) United States Patent
Argentine et al.

(10) Patent No.: US 11,938,249 B2
(45) Date of Patent: Mar. 26, 2024

(54) COATED ENDOVASCULAR PROSTHESES FOR ANEURISM TREATMENT

(71) Applicant: Medtronic Vascular, Inc., Santa Rosa, CA (US)

(72) Inventors: Jeffery Argentine, Petaluma, CA (US); Matt Petruska, Windsor, CA (US); Keith Perkins, Santa Rosa, CA (US); Samuel Robaina, Novato, CA (US); Darren Galligan, San Francisco, CA (US); Rajesh Radhakrishnan, Petaluma, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 900 days.

(21) Appl. No.: 16/928,080

(22) Filed: Jul. 14, 2020

(65) Prior Publication Data
US 2020/0338239 A1 Oct. 29, 2020

Related U.S. Application Data

(62) Division of application No. 15/621,637, filed on Jun. 13, 2017, now abandoned.
(Continued)

(51) Int. Cl.
*A61L 27/56* (2006.01)
*A61F 2/06* (2013.01)
(Continued)

(52) U.S. Cl.
CPC ............... *A61L 27/56* (2013.01); *A61F 2/06* (2013.01); *A61F 2/07* (2013.01); *A61L 27/52* (2013.01); *A61L 27/54* (2013.01); *A61L 27/58* (2013.01); *A61L 31/10* (2013.01); *A61L 31/16* (2013.01); *A61F 2002/072* (2013.01);
(Continued)

(58) Field of Classification Search
CPC .. A61L 27/56; A61L 31/10; A61F 2/06; A61F 2/07
See application file for complete search history.

(56) References Cited

U.S. PATENT DOCUMENTS 5,665,117 A   9/1997  Rhodes
5,693,088 A   12/1997 Lazarus
(Continued)

FOREIGN PATENT DOCUMENTS

CN   101917931 A   12/2010
CN   103889472 A   6/2014
(Continued)

OTHER PUBLICATIONS

PCT/US2017/024496, The International Search Report and The Written Opinion of the International Searching Authority, dated Jun. 28, 2017. 13 pgs.
(Continued)

*Primary Examiner* — Matthew W Schall

(57) ABSTRACT

The present technology relates generally to endovascular prostheses. More particularly, the disclosure relates to endovascular prostheses having an outer surface of a graft material thereof associated with a hydrogel composition, which may swell upon implantation within a blood vessel, thereby mediating various complications associated with endovascular procedures. The hydrogel compositions can also include various stabilizing polymers and active agents to further aid their use in the body.

22 Claims, 8 Drawing Sheets

Related U.S. Application Data

(60) Provisional application No. 62/352,626, filed on Jun. 21, 2016.

(51) Int. Cl.
| | |
|---|---|
| *A61F 2/07* | (2013.01) |
| *A61L 27/52* | (2006.01) |
| *A61L 27/54* | (2006.01) |
| *A61L 27/58* | (2006.01) |
| *A61L 31/10* | (2006.01) |
| *A61L 31/16* | (2006.01) |

(52) U.S. Cl.
CPC . *A61F 2002/077* (2013.01); *A61F 2210/0061* (2013.01); *A61L 2300/42* (2013.01)

(56) References Cited

U.S. PATENT DOCUMENTS

| | | | |
|---|---|---|---|
| 5,843,160 | A | 12/1998 | Rhodes |
| 6,395,019 | B2 | 5/2002 | Chobotov |
| 7,192,441 | B2 | 3/2007 | Sherry |
| 7,442,205 | B2 | 10/2008 | Verhoeven et al. |
| 7,682,383 | B2 | 3/2010 | Robin |
| 7,766,959 | B2 | 8/2010 | Dimatteo et al. |
| 7,955,372 | B2 | 6/2011 | Butterwick et al. |
| 2001/0027338 | A1 | 10/2001 | Greenberg |
| 2004/0098076 | A1 | 5/2004 | Rolando et al. |
| 2004/0098097 | A1 | 5/2004 | Fogarty et al. |
| 2004/0204755 | A1 | 10/2004 | Robin |
| 2004/0230289 | A1 | 11/2004 | Dimatteo et al. |
| 2004/0230389 | A1 | 11/2004 | Adler et al. |
| 2006/0149364 | A1 | 7/2006 | Walak et al. |
| 2006/0178733 | A1 | 8/2006 | Pinchuk et al. |
| 2007/0074481 | A1 | 4/2007 | Stoller |
| 2007/0244544 | A1 | 10/2007 | Birdsall et al. |
| 2008/0188923 | A1 | 8/2008 | Chu |
| 2009/0177265 | A1 | 7/2009 | Charlebois |
| 2010/0241214 | A1 | 9/2010 | Holzer et al. |
| 2011/0093058 | A1 | 4/2011 | Vardi |
| 2012/0123527 | A1 | 5/2012 | Isch |
| 2013/0245745 | A1 | 9/2013 | Vong et al. |
| 2013/0331929 | A1 | 12/2013 | Mitra et al. |
| 2015/0374516 | A1 | 12/2015 | Pereira et al. |
| 2017/0281331 | A1 | 10/2017 | Galligan |

FOREIGN PATENT DOCUMENTS

| | | |
|---|---|---|
| CN | 104244866 A | 12/2014 |
| CN | 108601647 A | 9/2018 |
| WO | 9939662 A1 | 8/1999 |
| WO | 03003945 A2 | 1/2003 |
| WO | 2006079006 A2 | 7/2006 |
| WO | 2008112757 A2 | 9/2008 |
| WO | 2009085186 A1 | 7/2009 |
| WO | 2013/033791 A1 | 3/2013 |
| WO | 2013/162682 A1 | 10/2013 |

OTHER PUBLICATIONS

PCT/US2017/037268, The International Search Report and The Written Opinion of the International Searching Authority, dated Sep. 12, 2017. 16 pgs.
Office Action from U.S. Appl. No. 15/471,078 dated Dec. 3, 2018.
Office Action from U.S. Appl. No. 15/471,078, dated Jul. 29, 2019.
Office Action dated Jun. 2, 2020 in Chinese Application No. 201780038223.9.

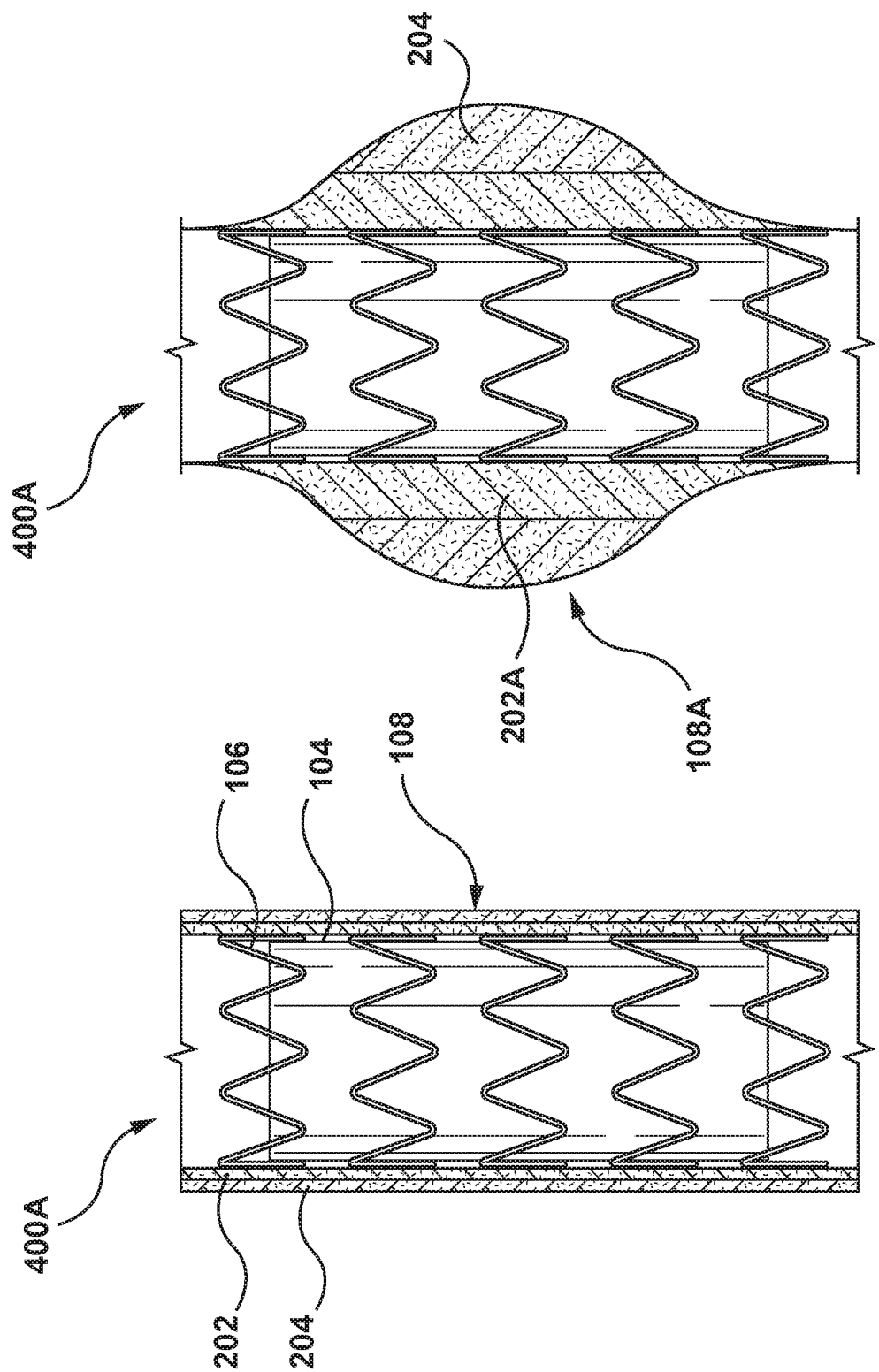

COATED ENDOVASCULAR PROSTHESES FOR ANEURISM TREATMENT

CROSS-REFERENCE TO RELATED APPLICATIONS

This application is a divisional of U.S. application Ser. No. 15/621,637, filed. Jun. 13, 2017, which claims the benefit of U.S. Provisional Application No. 62/352,626, filed Jun. 21, 2016, the disclosures of each of which are incorporated by reference herein in their entireties.

FIELD OF THE INVENTION

The present technology relates generally to endovascular prostheses. More particularly, the disclosure relates to endovascular prostheses having an outer surface of a graft material thereof associated with a hydrogel composition, which may swell upon implantation within a blood vessel, thereby mediating various complications associated with endovascular procedures. The hydrogel compositions can also include various stabilizing polymers and active agents to further aid their use in the body.

BACKGROUND OF THE INVENTION

Endovascular procedures have been successfully used to treat thoracic and abdominal aneurysms. Such procedures typically require intravascular delivery of a stent graft to the site of the aneurysm. The graft is then expanded or deployed in situ and one or more ends of the graft are anchored to the body lumen, suitably on each side of the aneurysm. In this way, the graft effectively excludes the aneurysm sac from circulation.

One concern with many conventional stent graft assemblies, however, is the long term durability of such structures. Over time, the graft can become separated from an inner surface of the body lumen, resulting in bypassing of the blood between the vessel wall and the graft. Termed an endoleak, this bypassing results in a persistent blood or other fluid flow outside the lumen of the stent graft, but within the aneurysm sac or adjacent vascular segment being treated by the device. When an endoleak occurs, it can cause continuous pressurization of the aneurysm sac and may result in an increased risk of rupture.

In addition to endoleaks, another concern with many conventional endovascular graft assemblies is subsequent device migration and/or dislodgement. For example, after a surgeon has found an optimal location for the graft, the device is preferably fixed to the wall of the body lumen and fully sealed at each end of the graft to prevent endoleaks and achieve a degree of fixation that will prevent subsequent device migration and/or dislodgement. An additional concern relates to the ability of stent gratis to seal in short neck aneurysms.

BRIEF SUMMARY OF THE INVENTION

In view of the foregoing, provided herein are devices and methods for providing a hydrogel composition to a treatment site of a blood vessel of a patient so as to mediate these complications.

Embodiments hereof are directed to an endovascular prosthesis having a compressed configuration for delivery within a vasculature and a radially-expanded configuration for deployment within a target blood vessel of a patient. Suitably, the endovascular prosthesis comprises an anchor stent for engaging an inner wall of the target blood vessel when the prosthesis is in the radially-expanded configuration, a tubular body formed from a graft material defining a central lumen from a first end to a second end thereof, wherein the anchor stent is attached to the first end of the tubular body, the tubular body having an inner surface and an outer surface, a body stent attached to the outer surface of the tubular body for maintaining the tubular body in the radially-expanded configuration, and a hydrogel composition associated with about 20% to about 100% of the outer surface of the tubular body. The hydrogel composition suitably comprises a hydrogel polymer and one or more of a stabilizing polymer, a biologically active agent and a bioabsorbable polymer. In embodiments, the hydrogel composition is in a non-expanded state and capable of expanding to an expanded state following introduction into the target blood vessel of the patient.

In further embodiments, provided herein is an endovascular prosthesis comprising a tubular body formed from a graft material, the tubular body having an inner surface and an outer surface, and a hydrogel composition associated with at least a portion of the outer surface of the tubular body. In embodiments, the hydrogel composition in a non-expanded state and capable of expanding to an expanded state following introduction into a target blood vessel of a patient.

Also provided herein are methods of delivering a hydrogel-associated endovascular prosthesis to a target blood vessel of a patient. The methods suitably comprise providing a hydrogel-associated endovascular prosthesis having a compressed configuration for delivery within a vasculature and a radially-expanded configuration for deployment within the target blood vessel. The prosthesis comprises an anchor stent for engaging an inner wall of the target blood vessel when the prosthesis is in the radially-expanded configuration, a tubular body formed from a graft material defining a central lumen from a first end to a second end thereof, wherein the anchor stent is attached to the first end of the tubular body, the tubular body having an inner surface and an outer surface, a body stent attached to the outer surface of the tubular body for maintaining the tubular body in the radially-expanded configuration, and a hydrogel composition associated with about 20% to about 100% of the outer surface of the tubular body. The hydrogel composition suitably comprises a hydrogel polymer and one or more of a stabilizing polymer, a biologically active agent and a bioabsorbable polymer, wherein the hydrogel composition in a non-expanded state and capable of expanding to an expanded state following introduction into the target blood vessel of the patient. The methods further comprise introducing the hydrogel-associated endovascular prosthesis transluminally into a selected portion of the target blood vessel, wherein the hydrogel composition is in the non-expanded state. Further, the methods comprise radially expanding the endovascular prosthesis into contact with the target blood vessel, and expanding the hydrogel composition to the expanded state within the target blood vessel.

In still further embodiments, provided herein are methods of mediating a complication during an endovascular treatment of a target blood vessel of a patient. The methods suitably comprise providing an endovascular prosthesis having a compressed configuration for delivery within a vasculature and a radially-expanded configuration for deployment within the target blood vessel. The prosthesis comprises an anchor stent for engaging an inner wall of the target blood vessel when the prosthesis is in the radially-expanded configuration, a tubular body, formed from a graft material defining a central lumen from a first end to a second end thereof, wherein the anchor stent is attached to the first end of the tubular body, the tubular body having an inner surface and an outer surface, a body stent attached to the outer surface of the tubular body for maintaining the tubular body in the radially-expanded configuration, and a hydrogel composition associated with about 20% to about 100% of the outer surface of the tubular body. Suitably, the hydrogel composition comprises a hydrogel polymer and one or more of a stabilizing polymer, a biologically active agent and a bioabsorbable polymer, wherein the hydrogel composition in a non-expanded state and capable of expanding to an expanded state following introduction into the target blood vessel of the patient. The methods further comprise introducing the endovascular prosthesis transluminally into a selected portion of the target blood vessel, wherein the hydrogel composition is in the non-expanded state, radially expanding the endovascular prosthesis into contact with the target blood vessel, and expanding the hydrogel composition to the expanded state within the target blood vessel, thereby mediating the complication.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The components in the drawings are not necessarily to scale.

FIGS. 4A-4B are sectional views showing the expansion of a hydrogel composition associated with an endovascular prosthesis as described in further embodiments hereof.

DETAILED DESCRIPTION OF THE INVENTION

Specific embodiments of the present technology are now described with reference to the figures, wherein like reference numbers indicate identical or functionally similar elements. Unless otherwise indicated, the terms "distal" and "proximal" are used in the following description with respect to the direction of blood flow from the heart and through the vasculature. Accordingly, with respect to a prosthesis or stent, the terms "proximal" and "distal" can refer to the location of portions of the device with respect to the direction of blood flow. For example, proximal can refer to an upstream position or a position of blood inflow, and distal can refer to a downstream position or a position of blood outflow. For example, "distal" or "distally" indicates an apparatus portion distant from, or a direction away from, the heart or along the vasculature in the direction of blood flow. Likewise, "proximal" and "proximally" indicates an apparatus portion near to, or in a direction towards the heart.

The following detailed description is merely exemplary in nature and is not intended to limit the present technology or the application and uses of the present technology. Although the description of embodiments hereof are in the context of treatment of tissue defects in blood vessels, the present technology may also be used in any other body passageways or other blood vessel locations not specifically discussed herein and where it is deemed useful (e.g., other anatomical lumens, such as bronchial and other air passageways, fallopian tubes, bile ducts, etc.). Furthermore, there is no intention to be bound by any expressed or implied theory presented in the preceding technical field, background, brief summary or the following detailed description.

Embodiments of the present technology as described herein can be combined in many ways to treat one or more of many vascular defects such as aneurysms or dissections within a blood vessel, such as the abdominal or thoracic regions of the aorta. The embodiments of the present technology can be therapeutically combined with many known surgeries and procedures, for example, such embodiments can be combined with known methods of accessing the target tissue defects, such as percutaneous access of the abdominal or thoracic regions of the aorta through the femoral artery to deliver and deploy the endoluminal prosthetic devices described herein. Other routes of access to the target regions are also contemplated and are well known to one of ordinary skill in the art.

Endovascular Prostheses Comprising Hydrogel Compositions

Figure 1A:
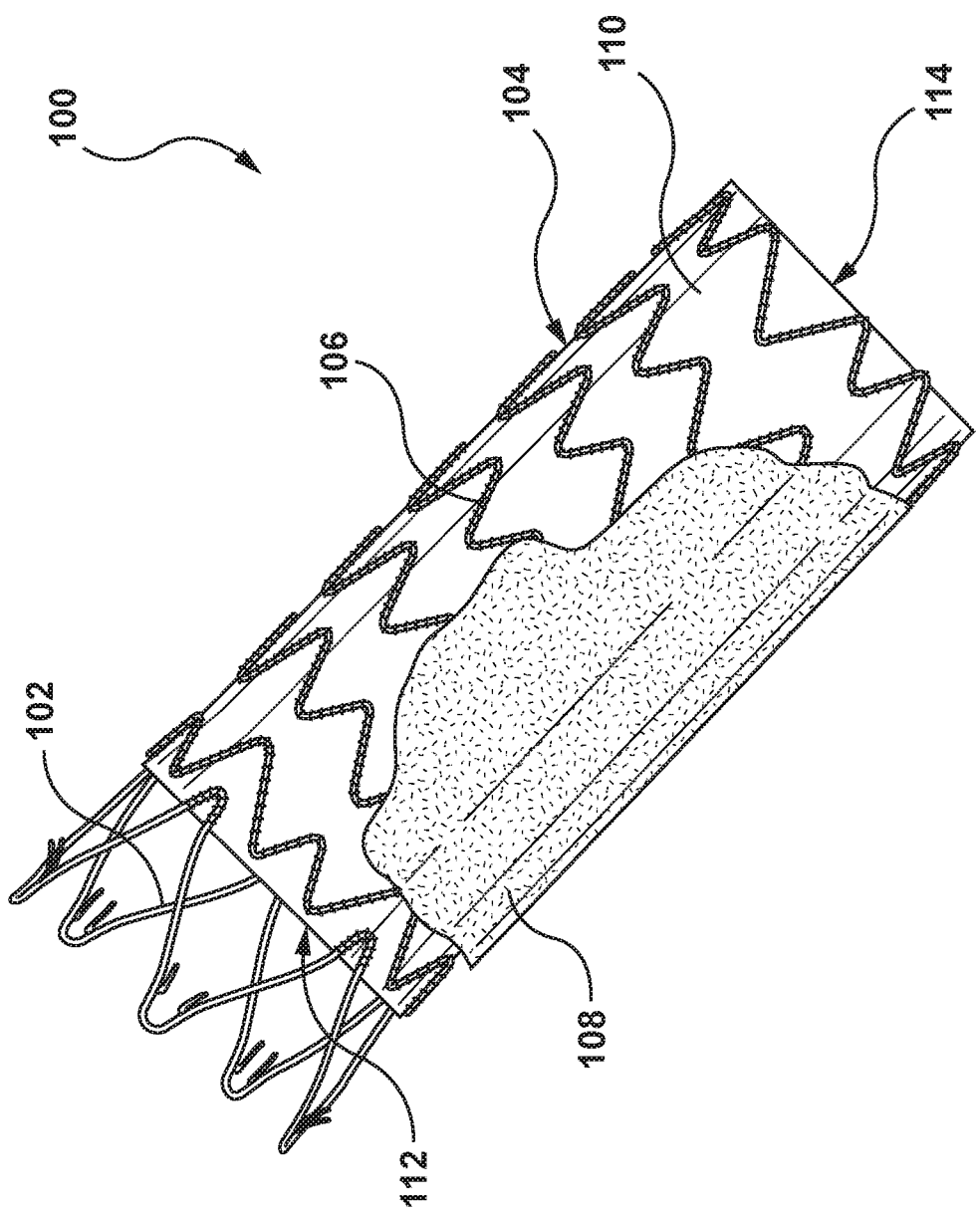
FIG. 1A is an endovascular prosthesis in accordance with an embodiment hereof.
Figure 1B:
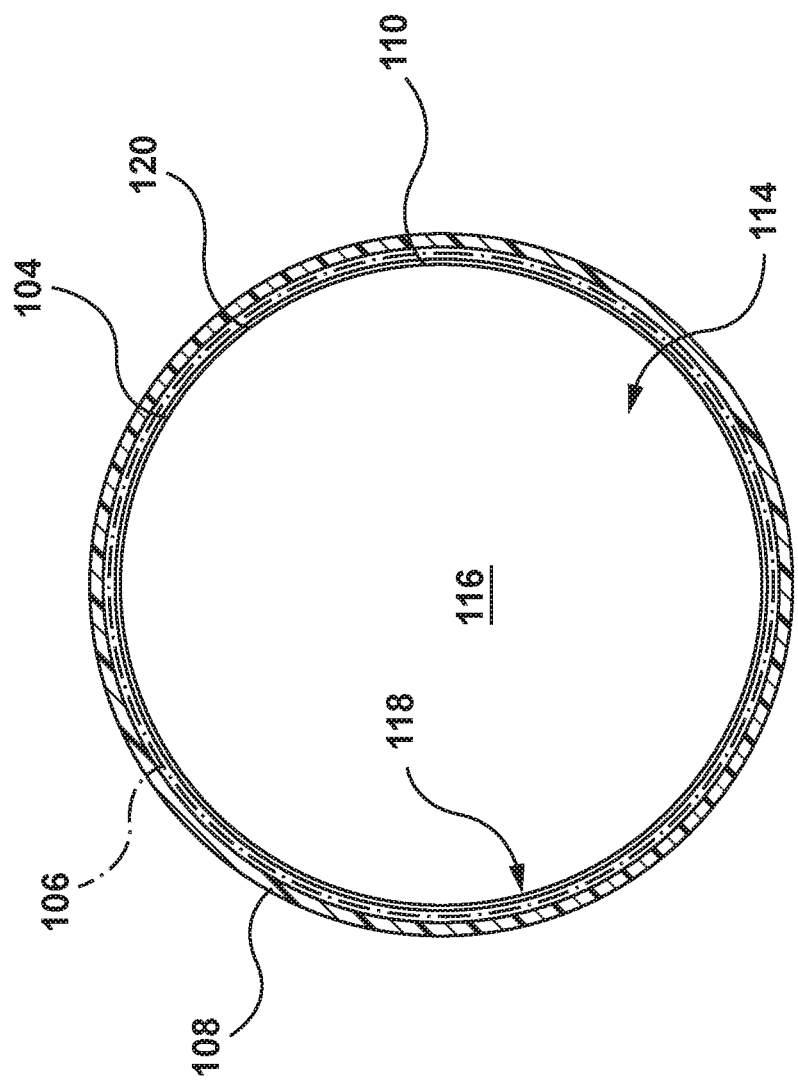
FIG. 1B is a sectional view of an endovascular prosthesis in accordance with an embodiment hereof.

In embodiments, described herein are endovascular prostheses. For example, as shown in FIG. 1A, endovascular prosthesis 100 suitably comprises a tubular body 104 formed from a graft material 110. As shown in FIG. 1B, tubular body 104 has an inner or luminal surface 118 and an outer or abluminal surface 120. A hydrogel composition 108 is suitably associated with at least a portion of the outer surface 120 of tubular body 104. In embodiments, endovascular prosthesis 100 can further comprise one or more body stents 106.

In an embodiment, tubular body 104 is suitably cylindrical in shape. In embodiments, tubular body 104 has a uniform cross-sectional diameter (see, FIG. 1B), though in other embodiments, tubular body 104 can have a diameter that increases or decreases over the length of the structure, either uniformly or non-uniformly. In embodiments, for example, tubular body 104 can have a larger diameter at one end and a smaller diameter at an opposite end. In embodiments, tubular body 104 is a single tube, though in other embodiments, it can have two or more tubular sections, and can be composed of as single structure or multiple structures.

As used herein "hydrogel composition" refers to a composition which comprises a hydrogel polymer, and suitably further comprises one or more additional materials as described herein. Hydrogel composition 108 can be a solution, gel, foam or other material which can be readily associated with the graft material of tubular body 104.

A "hydrogel polymer" is a 3-dimensional network of cross-linked, hydrophilic macromolecules capable of being swelled and incorporating about 20 percent to about 95 percent water by weight. Examples of natural hydrogel polymers include fibrin, collagen, elastin, and the like.

Hydrogel compositions, in some instances, are capable of absorbing water (or other fluid, e.g., blood) relative to its dry weight to greater than 50%, greater than 75%, greater than 100%, greater than 150%, etc. of its dry weight. In other embodiments, the hydrogel composition may be fully hydrated when containing less than 50% of its dry weight (e.g., less than 45%, less than 40%, etc.). In a dehydrated or low volume state, a hydrogel composition can, in some instances, be fairly rigid; however with certain compositions, the hydrogel composition can exhibit increased flexibility as water content increases.

Hydrogel composition 108 may include a variety of hydrogel polymers, or other appropriate hydrophilic or hydrophobic materials, as well as other suitable materials, such as foams, interpenetrating polymer networks and thermosets. Such materials are described herein as examples, and these and other materials will be apparent to those of ordinary skill in the art. Exemplary hydrogel polymers include polyethylene oxide, polyvinyl alcohol, polyacrylic acid, polypropylene fumarate-co-ethylene glycol, and polypeptides. Agarose, alginate, chitosan, collagen, fibrin, gelatin, and hyaluronic acid are naturally-derived polymers that can also be used for this purpose. For example, hydrogel polymers suitably comprise poly(hydroxyethyl methacrylate), poly-2-hydroxy ethylmethacrylate (p-HEMA) and copolymers thereof, poly (vinylpyrrolidinone) (PVP), poly-N-vinyl-pyrrolidone (pNVP) hydrogels, pHEMA/pNVP copolymer, polyvinylalcohol (PVA) hydrogels, poly(acrylamide) (pAM), poly(acrylic acid) (pAA), and other similar materials.

As described herein, hydrogel composition 108 is suitably associated with at least a portion of the outer surface 120 of tubular body 104. For example hydrogel composition 108 can be coated on the outer surface 120 of tubular body 104, or impregnated into or otherwise made a part of the graft material 110 of tubular body 104. In embodiments, hydrogel composition 108 can be sprayed (spray coating), spin-coated (electrospinning), layer, printed, painted, rolled, or otherwise coated onto the graft material 110. The graft material 110 can also be dipped into a solution, slurry or suspension of hydrogel composition 108 so as to coat the graft material 110 (dip coating). In other embodiments, it is possible to co-form hydrogel composition 108 and the graft material 110 together so as to prepare an integrated hydrogel composition-graft material structure. The hydrogel composition can be associated with the tubular body 104 (suitably graft material 110 of the tubular body), either before or after the tubular body 104 is formed. That is, the hydrogel composition 108 can be applied to a graft material 110, after which the material is formed into the structure of the tubular body 104. In other embodiments, the hydrogel composition 108 can be associated with the graft material 110 after the tubular body 104 is formed, but before any body stents 106 are added. In still further embodiments, the tubular body 104, including body stent 106, can first be formed, and then hydrogel composition 108, applied to the outer surface 120.

In embodiments, the hydrogel composition 108 is applied to the tubular body 104 in a liquid, gel, foam, suspension other flowable form, and then subsequently dried, cured, or otherwise associated with the tubular body 104 so as to provide a final product which can be stored and manipulated.

Suitably, the hydrogel composition 108 is associated with only the outer surface 120 of tubular body 104. However, in some embodiments, all or a portion of the inner surface 118 of tubular body 104 can also have the hydrogel composition associated with it. Suitably, the hydrogel composition is associated with less than 20% of the inner surface of tubular body, more suitably less than 10%, less than 5%, less than 1%, and even more suitably, about 0% of the tubular body.

In exemplary embodiments, the hydrogel composition 108 is associated with at least a portion of the outer surface 120 of tubular body 104. This can include as little as 1-10% of the outer surface 120 of the tubular body, up to and including 95-100% of the outer surface. The percentage of coverage of tubular body 104 by hydrogel composition 108 is suitably expressed as a percent area, when measuring the surface area of the tubular body. The surface area of the tubular body 104 can be calculated as all of the outer surface of the entire endovascular prosthesis (i.e., over the entire length of the tubular body), or can be calculated based on the area of the endovascular prosthesis which is, or will be, in contact with a specific target area of a vessel. In embodiments, hydrogel composition 108 is associated with about 1% to about 100% of the outer surface tubular body 104, measured based on the entire surface of the tubular body, suitably about 10% to about 100%, or about 20% to about 100%, about 30% to about 100%, about 40% to about 100%, about 50% to about 100%, about 60% to about 100%, about 70% to about 100%, about 80% to about 100%, about 90% to about 100%, about 1% to about 50%, about 10% to about 40%, about 10% to about 40%, about 20% to about 40%, about 30% to about 90%, about 30% to about 80%, about 40% to about 90%, about 50% to about 90%, about 60% to about 90%, about 70 to about 90%, about 80% to about 90%, about 10%, about 20%, about 30%, about 40%, about 50%, about 60%, about 70%, about 80%, about 90% or about 100%, of hydrogel composition 108 is associated with the outer surface of tubular body 104. In still further embodiments, hydrogel composition 108 is associated with about 1% to about 100% of the outer surface tubular body 104, measured based on the specific target area of the endovascular prosthesis, for example a portion that will contact a neck region of an aneurysmal sac. For example, suitably about 10% to about 100%, or about 20% to about 100%, about 30% to about 100%, about 40% to about 100%, about 50% to about 100%, about 60% to about 100%, about 70% to about 100%, about 80% to about 100%, about 90% to about 100%, about 30% to about 90%, about 30% to about 80%, about 40% to about 90%, about 50% to about 90%, about 60% to about 90%, about 70% to about 90%, about 80% to about 90%, about 50%, about 60%, about 70%, about 80%, about 90% or about 100%, of hydrogel composition 108 is associated with the outer surface of tubular body 104, measured over a specific area of tubular body 104.

Suitably prior to implantation of the endovascular prosthesis 100, such as during storage, handling and delivery to a treatment site, hydrogel composition 108 is in a non-expanded state and capable of expanding to an expanded state following introduction into or implantation within a target blood vessel of a patient. By associating tubular body 104 with hydrogel composition 108, when the endovascular prosthesis is introduced in a target blood vessel, water/blood is able to be absorbed within the hydrogel composition and hydrate the hydrogel polymer. In a "non-expanded state" the hydrogel composition suitably contains less than 10% by weight water. When contacted with water (e.g., blood), the hydrogel composition swells or expands to an "expanded state," thereby occupying a larger volume than in its non-expanded state. In this "expanded state" the expanded hydrogel composition 108A is able to fill an empty volume, such as an aneurysmal sac, or neck region of an aneurysmal sac surrounding tubular body 104, and in some instances, can compress tissue or other structures which surround the endovascular prosthesis 100.

In further embodiments, hydrogel composition 108 can further comprise a stabilizing polymer. As used herein "stabilizing polymer" refers to a polymer which provides an additional structure to the hydrogel composition, such that expansion of the hydrogel polymer is limited or constrained. The addition of a stabilizing polymer suitably helps to prevent embolization of the hydrogel composition. The stabilizing polymer can be a co-mixture with the hydrogel polymer, or can be coated under or suitably on top of the hydrogel polymer (i.e., with polymer hydrogel directly contacting the graft material of tubular body 104). Exemplary stabilizing polymers include various biocompatible polymers, including for example, poly(ethylene terephthalate) and poly(urethane).

As shown in FIG. 1A, hydrogel composition 108 suitably forms a hydrogel coating on at least a portion of the outer surface 120 of the tubular body 104. This coating or layer, is shown in FIGS. 1A and 1B by way of illustration and not limitation, and is not meant to imply a specific structure for the hydrogel composition.

In embodiments, hydrogel composition 108 (or hydrogel coating) covers the entire outer surface 120 of the tubular body 104. This includes both the graft material 110 of tubular body 104, as well as body stents 106, show in FIG. 1A. In other embodiments, body stents 106 may not be covered with hydrogel composition 108, but may be completely free of hydrogel composition 108, or have some portion of hydrogel composition touching or partially covering the body stents 106. Methods of preparing a hydrogel composition that only associates with the graft material can include the use of masking materials on the structures of body stents 106 that will repel the application of a hydrogel composition, or a material which can be removed to also remove a hydrogel composition coating thereon.

Figure 2:
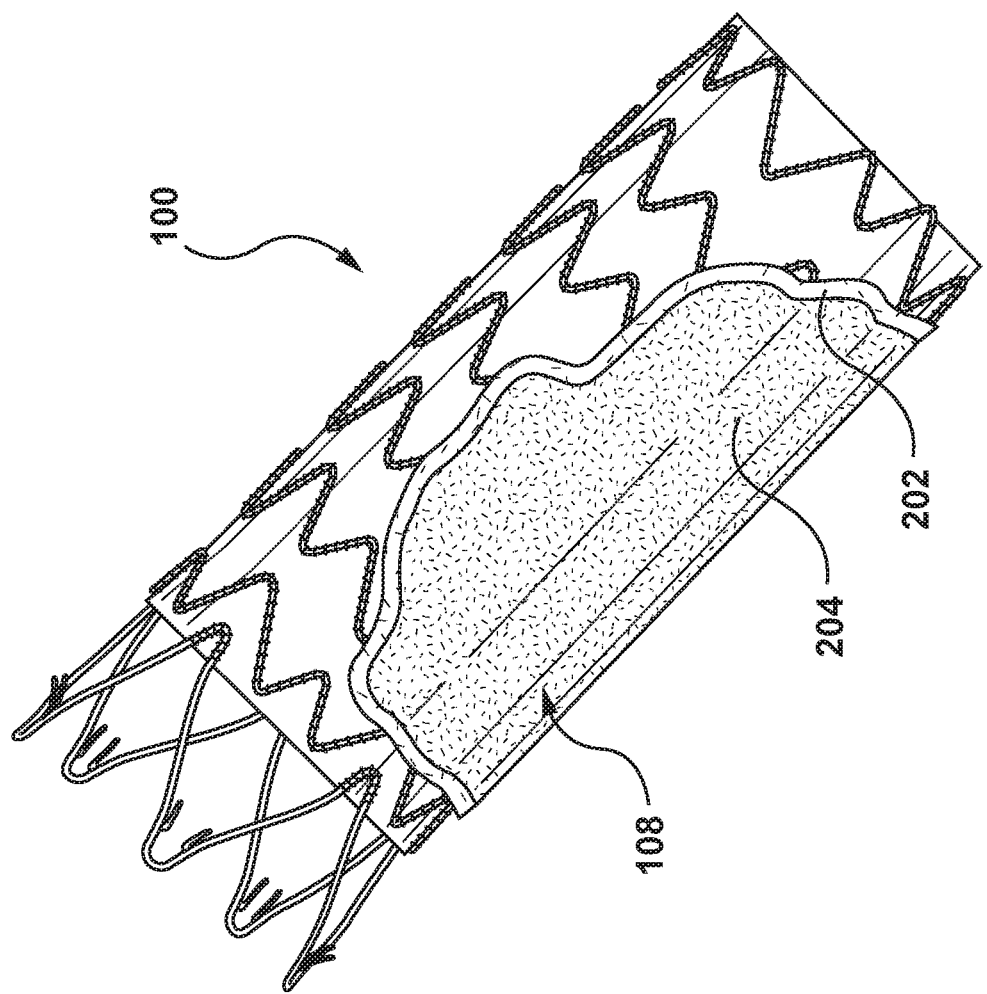
FIG. 2 is an endovascular prosthesis in accordance with another embodiment hereof.

FIG. 2 illustrates an endovascular prosthesis 100 comprising a hydrogel composition 108 comprising a first or inner layer 202 which is in direct contact with the graft material 110 of tubular body 104 and a second or outer layer 204, on top of first layer 202. Additional layers of hydrogel composition beyond 2 layers can also be used so as to generate a multi-layer structure (e.g., 3, 4, 5, 6, 7, 8, 9, 10, etc., layers). For example, first layer 202 can comprise a hydrogel polymer as described herein, while second layer 204, can comprise a stabilizing polymer, or other composition as described herein (e.g., a bioactive agent layer and/or bioabsorbable polymer layer).

Figure 3B:
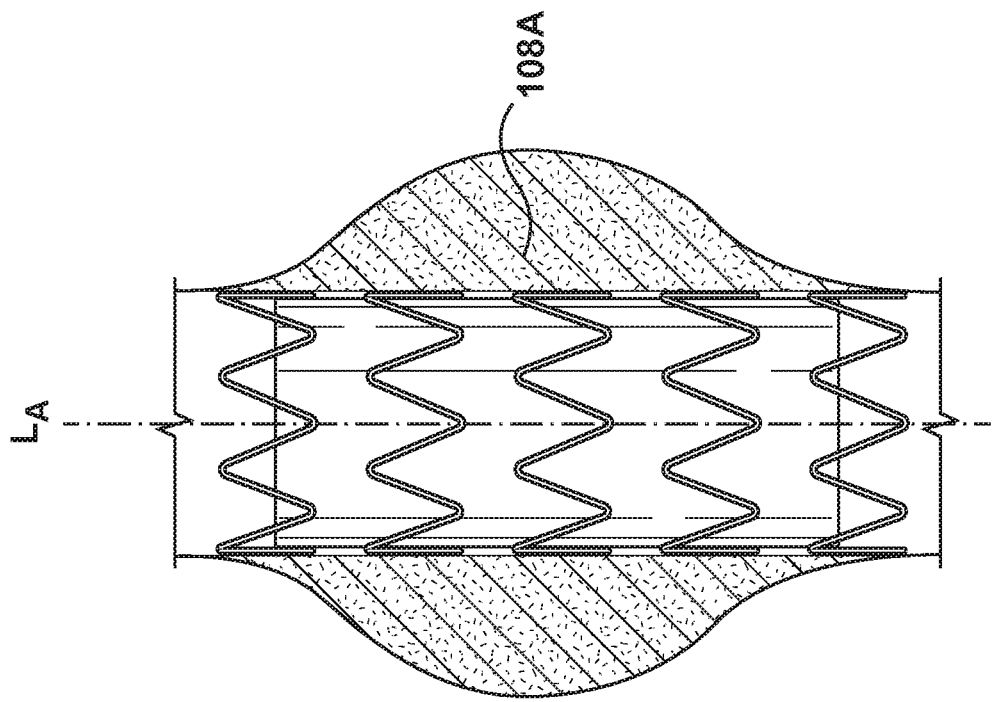
FIGS. 3A-3B are sectional views showing the expansion of a hydrogel composition associated with an endovascular prosthesis as described in embodiments hereof.
Figure 3A:
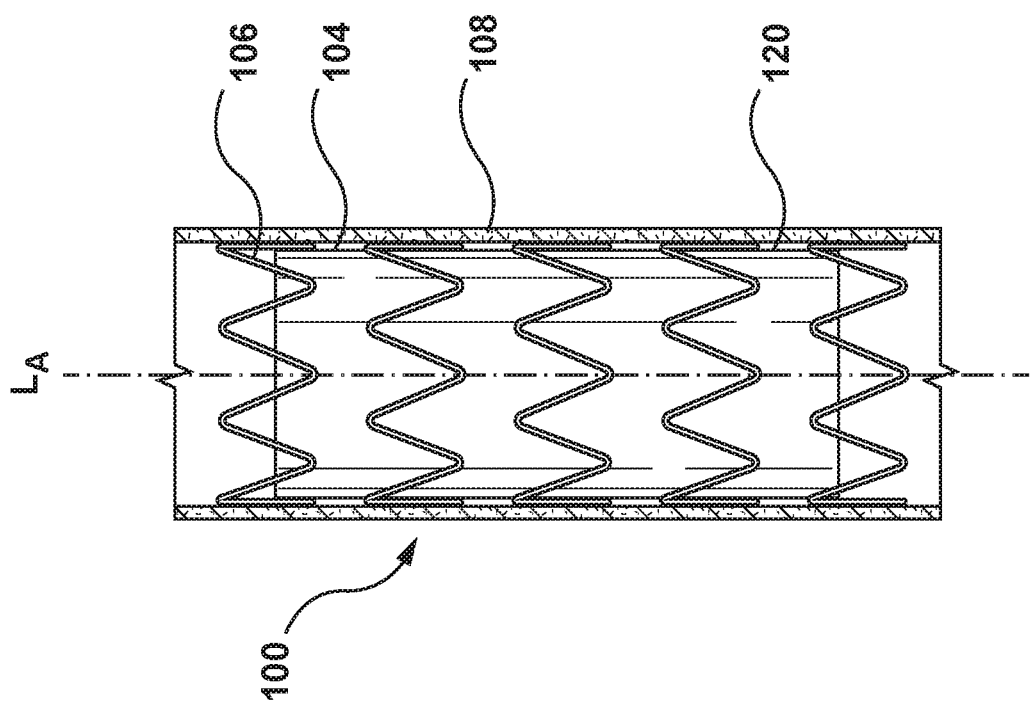

FIG. 3A shows a section view of an exemplary endovascular prosthesis 100 as described herein. As shown, tubular body 104 comprises a hydrogel composition 108 associated with an outer surface 120 thereof. Hydrogel composition 108 is in a non-expanded state. This state can correspond to a pre-insertion state, in which, for example, the endovascular prosthesis is removed from a suitable packaging and readied for use (for example, introduction into a patient). Hydrogel composition 108 is suitably associated with tubular body 104 in such a way (i.e., as a coating) that it does not easily separate or become removed from the tubular body, but rather, remains associated with the tubular body 104 so that the endovascular prosthesis 100 can be manipulated, bent, or otherwise prepared for insertion.

FIG. 3B shows the same endovascular prosthesis 100 of FIG. 3A, after the hydrogel composition has been contacted with water, blood, or other aqueous solution, so that the hydrogel polymer of the hydrogel composition 108 swells to expanded hydrogel composition 108A in an expanded state. Hydrogel composition 108 suitably expands radially away from a longitudinal or central axis $L_A$ of tubular body 104. In embodiments, the magnitude of expansion is relatively uniform over the entire area which is covered by hydrogel composition. In other embodiments, however, hydrogel composition 108 can be applied or otherwise structured so as to expand more over a particular area, e.g., at the center of the length of endovascular prosthesis.

As described herein, a suitable hydrogel composition 108 is associated with tubular body 104 in a uniform manner, i.e., having a fairly uniform thickness along the length of the tubular body that is coated. In exemplary embodiments, the average dry coating thickness (T) of the hydrogel composition is about 0.1 micrometer to about 25 microns, with a standard deviation ($\sigma$), and a relative standard deviation ($100 \times \sigma/T$) of no greater than about 10 percent. In further embodiments, hydrogel composition 108 can comprise multiple layers (e.g., hydrogel polymer and stabilizing polymer), each having a thickness within this recited range of about 0.1 to about 25 microns.

In still further embodiments, hydrogel composition 108 can further comprise a biologically active agent. As used herein "biologically active agent" refers to a composition or substance that has an effect on living tissue. Biologically active agents include, for example, therapeutic agents, which are substances that tend to prevent and/or overcome disease and/or promote recovery. As such, biologically active agents also include, for example, biologically active molecules (biomolecules) such as drugs. In exemplary embodiments, the biologically active agents which can be utilized in the embodiments described herein include, but are not limited to, collagen, fibrin, thrombin, dipyridamole, heparin, anti-platelet drugs, anti-thrombogenic drugs, anti-proliferative drugs, and anti-mitotic drugs. Suitably, the biologically, active agent is a pro-thrombotic material such as collagen fibrin or thrombin. Exemplary bioactive agents are disclosed in U.S. Pat. No. 7,442,205, the disclosure of which is incorporated by reference herein in its entirety, and which is adapted to the various embodiments herein.

Biologically active agents can be utilized with the endovascular prosthesis by adding the biologically active agent to a hydrogel polymer solution prior to applying, or by applying the biologically active agent to a hydrogel polymer layer already associated with the outer surface of a tubular body. If the biologically active agent is applied to a hydrogel polymer on a tubular body, the application may take place either before or after the tubular body has been fabricated into a final endovascular prosthesis. The biologically active agent may be applied in either a dry, or the wet state. Application of the biologically active agent in the wet or swollen state suitably provides for more uniform distribution throughout the hydrogel composition. Suitable application methods include, for example, dip coating. Biologically active agents may be added to endovascular prostheses as described herein to provide, for example, biocompatible surfaces. When biologically active agents are used, they are typically added in about 0.1 percent by weight to about 25 percent by weight based on the weight of the hydrogel polymer that is utilized.

In further embodiments, hydrogel compositions may be selected and formulated to controllably release biologically active agents at a desired rate. The rate of release may depend on, for example, the amount and type of biologically active agent present in the compositions and the temperature and conditions of the desired release. The rate of release may also depend on the properties of the selected hydrogel polymer including, for example, solubility and polarity. Other factors may also affect the rate of release including, for example, crosslink density.

Biologically active agents may also be permanently attached to a hydrogel polymer using an appropriate amount and orientation effective to provide, for example, an improved nonthrombogenic surface relative to the substrate without the biologically active agent. In embodiments, relatively high biologically active agent loading capacities (often as high as 50 micrograms of biologically active agents per square centimeter of surface) and bioactivities (often as high as 1.0 International Unit (IU) thrombin (IIa) deactivated per square centimeter of modified surface) can be utilized.

In still further embodiments, hydrogel composition 108 can further comprise a bioabsorbable polymer. As used herein, a "bioabsorbable polymer" is a polymer which is readily degraded to components which can be easily adsorbed or otherwise cleared from the body. Examples of bioabsorbable polymers include, but are not limited to, polylactic-co-glycolic acid), polylactic acid) and poly(glycerol sebacate).

In embodiments, hydrogel composition 108 can comprise both a biologically active agent and a bioabsorbable polymer, along with a hydrogel polymer. In further embodiments, a hydrogel composition can comprise in addition to hydrogel polymer, any one or more of a stabilizing polymer, a biologically active agent and/or a bioabsorbable polymer. Various iterations of these combinations can be readily envisioned and prepared by a person of ordinary skill in the art.

As with the stabilizing polymer, bioactive agent and/or bioabsorbable polymer can be applied as a second layer over top of the hydrogel polymer of hydrogel composition 108 (see, e.g., FIG. 2), or suitably can be mixed together and co-applied to the outer surface 120 of tubular body 104 so as to form a hydrogel composition. By mixing the biologically active agent and/or bioabsorbable polymer with the hydrogel polymer, expansion of hydrogel polymer can enable the penetration of the biologically active agent and/or bioabsorbable polymer further into a thrombus, and hence increase the effective conversion of the thrombus into fibrocellular tissues. In addition, specific materials can be associated over the entirety of the outer surface of the tubular body, or only on selected areas of the outer surface. For example, materials that enable conversion of a thrombus to fibrocellular tissue (biologically active agent/bioabsorbable polymer) suitably may not be applied to an endovascular prosthesis in an area that may come in contact with a neck of an aneurysmal sac, but rather, formed primarily in the area that will contact a thrombus. Thus, suitably an outer coating or layer of hydrogel composition can comprise a material for promoting conversion of thrombus into fibro-cellular tissue formed on at least a portion of the tubular body 104 having the hydrogel polymer coating or layer. In an embodiment, the outer coating is not applied to end portions (112, 114) of the tubular body 104 that contact a wall of a vessel.

Figures 4C, 4D:
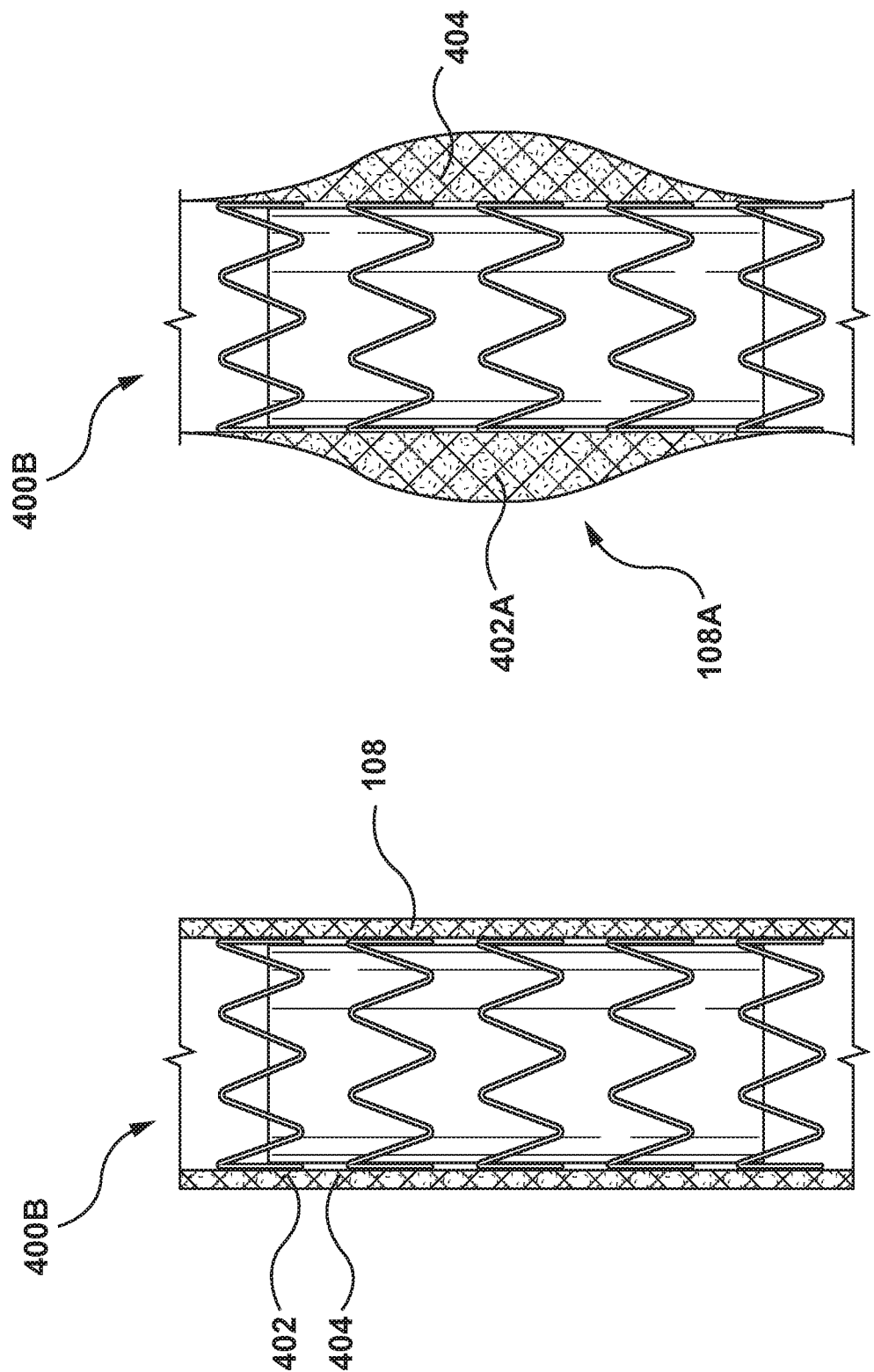
FIGS. 4C-4D are sectional views showing the expansion of a hydrogel composition associated with an endovascular prosthesis as described in still further embodiments hereof.

FIGS. 4A and 4B illustrate an embodiment of an endovascular prosthesis 400A in which the tubular body 104 has a hydrogel composition 108 that comprises a first layer 202, suitably a hydrogel polymer, and a second layer 204, suitably a biologically active agent (or a bioabsorbable polymer). In FIG. 4A, the hydrogel composition 108 is in a non-expanded state. Upon hydration with water (e.g., blood), the hydrogel polymer 202 of hydrogel composition 108 swells to expanded hydrogel composition 108A in an expanded state, while the biologically active agent 204 (and/or bioabsorbable polymer) remains associated with the expanded hydrogel polymer 202A, as shown in FIG. 4B. In a further embodiment, in FIG. 4C, an endovascular prosthesis 400B comprises a hydrogel composition 108 which contains both a hydrogel polymer 402 and a biologically active agent 404 (and/or bioabsorbable polymer) co-mixed with the hydrogel polymer. A non-expanded state of the hydrogel composition 108 is illustrated in FIG. 4C. Upon hydration with water (e.g., blood), the hydrogel composition swells to expanded hydrogel composition 108A in an expanded state comprising expanded hydrogel polymer 402A, while biologically active (and/or bioabsorbable polymer) agent 404 remains associated with the expanded hydrogel composition 108A, as shown in FIG. 4I).

It should be noted that the composition of hydrogel composition 108 need not be uniform throughout the entire length of tubular body 104 where it is associated. For example, certain sections of a tubular body in accordance with embodiments hereof can be associated with a hydrogel composition containing a hydrogel polymer only, while another section of the tubular body can be associated with a hydrogel composition containing a hydrogel polymer and a biologically active agent and/or bioabsorbable polymer. For example, sections of an endovascular prosthesis that come in contact with a neck of an aneurysmal sac, i.e., a proximal 112 or distal end 114, may contain only a hydrogel polymer (and possibly a stabilizing polymer), while sections 608 (see FIG. 6) that contact an aneurysm may also further contain a biologically active agent and/or bioabsorbable polymer.

Suitable graft materials for use in endovascular prostheses hereof, as the structure for tubular body 104, include polymeric materials, fabrics, metals, etc. In embodiments, a suitable graft material may be a flexible sheet of a material such as polytetrafluoroethylene (PTFE), expanded PTFE (ePTFE), ultra-high-molecular-weight polyethylene (UHMWPE), polyurethane, polyester and various mixtures and co-polymers thereof.

Also provided herein are endovascular prostheses having a compressed configuration for delivery within a vasculature, and a radially-expanded configuration for deployment within a target blood vessel of a patient. In exemplary embodiments, as shown in FIGS. 1A-1B, provided is an endovascular prosthesis 100 further comprising an anchor stent 102 for engaging an inner wall of a target blood vessel when the prosthesis is in the radially-expanded configuration. Suitably, endovascular prosthesis 100 further comprises a tubular body 104 formed from a graft material 110 defining a central lumen 116 from a first end 112 to a second end 114 thereof. Suitably anchor stent 102 is attached to the first end of the tubular body 104, the tubular body having an inner surface and an outer surface. Suitably, a body stent 106 is attached to the outer surface of the tubular body 104 for maintaining the tubular body in the radially-expanded configuration. Endovascular prosthesis 100 also suitably further comprises a hydrogel composition 108 associated with about 20% to about 100% of the outer surface of the tubular body. Suitably, hydrogel composition 108 comprises a hydrogel polymer and one or more of a stabilizing polymer, a biologically active agent and a bioabsorbable polymer.

As described herein, the hydrogel composition is in a non-expanded state and capable of expanding to an expanded state following introduction into the target blood vessel of the patient. Upon deployment within a target blood vessel, the hydrogel composition expands to an expanded state. This allows for the hydrogel composition to fill in volume external to the tubular body, and suitably, to mediate a complication associated with an endovascular procedure and/or to aid in sealing. Such complications include, for example, an endoleak and/or prosthesis migration, and/or may aid in sealing an end of the prosthesis when treating short neck aneurysms.

As described throughout, suitably the hydrogel composition comprises a hydrogel polymer, and in additional embodiments, can further comprise a stabilizing polymer. Additional embodiments are provided where the hydrogel composition comprises a hydrogel polymer, a stabilizing polymer and a biologically active agent. In still further embodiments, the hydrogel composition comprises a hydrogel polymer, a stabilizing polymer and a bioabsorbable polymer.

Exemplary hydrogel polymers, stabilizing polymers, biologically active agents and bioabsorbable polymers for use in the hydrogel compositions are described herein. Suitable graft materials for use in the endovascular prostheses are also described throughout.

Figure 5A:
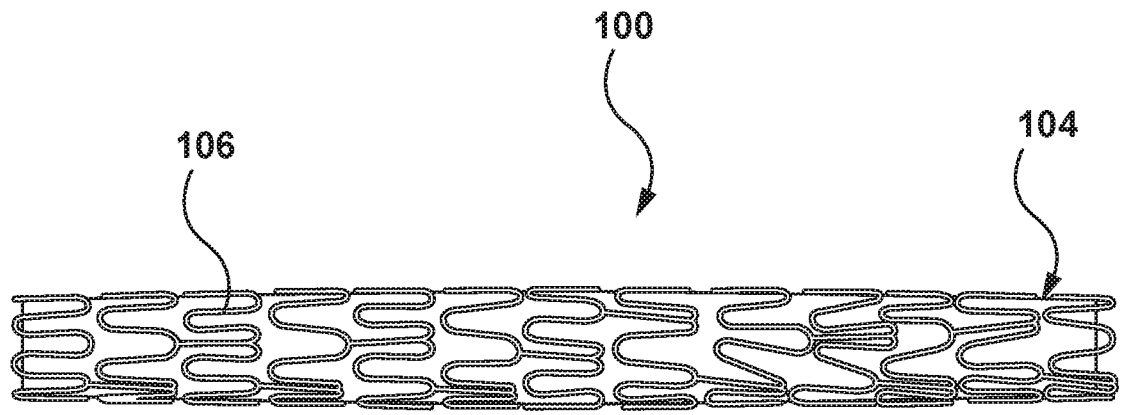
FIGS. 5A-5B show the transition of an endovascular prosthesis from a radially, compressed to radially expanded configuration.
Figure 5B:
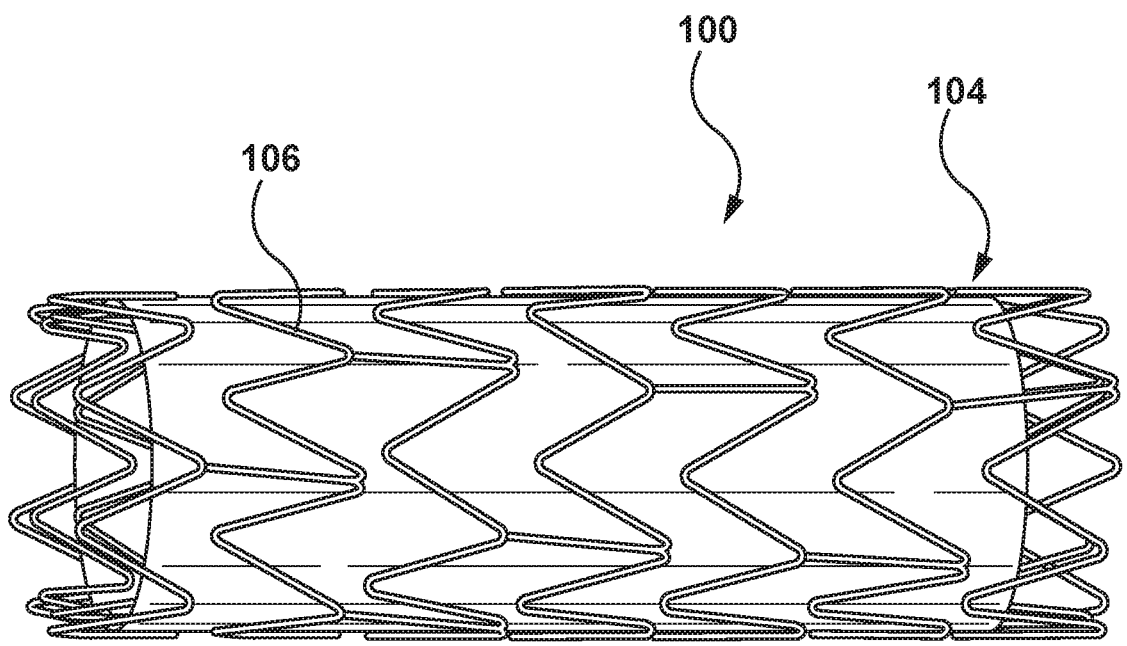

Suitable materials and methods of making an anchor stent and a body stent in accordance with embodiments hereof are known in the art. In embodiments hereof, body stent 106 allows for the endovascular prosthesis 100 to transition between a radially-compressed configuration (see FIG. 5A) suitable for delivery in a low-profile delivery catheter and a radially-expanded configuration (see FIG. 5B). FIGS. 5A-5B are show to illustrate the transition between a radially compressed configuration and a radially expanded configuration, and do not limit the structure for the endovascular prosthesis 100 described throughout. Body stents 106 can be provided as rings or other expandable features that can be self-expanding and/or balloon expandable as is known in the art. The term "self-expanding" is used to convey that the structures are shaped or formed from a material that can be provided with a mechanical memory to return the structure from a radially-compressed or constricted delivery configuration to a radially-expanded configuration for deployment. Non-exhaustive exemplary self-expanding materials include stainless steel, a super-elastic metal such as a nickel titanium alloy or nitinol, various polymers, or a so-called super alloy, which may have a base metal of nickel, cobalt, chromium, or other metal. Mechanical memory may be imparted to a wire or other stent structure, such as anchor stent 102, by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

In embodiments hereof, the endovascular prostheses can comprise the recited components, consist of the recited components (i.e., no other components may be included) or consists essentially of the recited components. In embodiments that consist essentially of the recited components, the endovascular prostheses described herein contain the specified materials and those that do not materially affect the basic and novel characteristics of the endovascular prostheses. Such materials that do not materially affect the basic and novel characteristics would include materials that do not impact the ability of the hydrogel composition associated with the tubular body of the endovascular prostheses to take up water, and expand to an expanded state, thus allowing the hydrogel composition to fill in external volume surrounding the tubular body of the endovascular prosthesis. Examples of such materials that do not materially affect the basic and novel characteristics may include other polymers, stabilizing agents, bioactive agents, etc.

Methods of Utilizing an Endovascular Prosthesis

Figure 6:
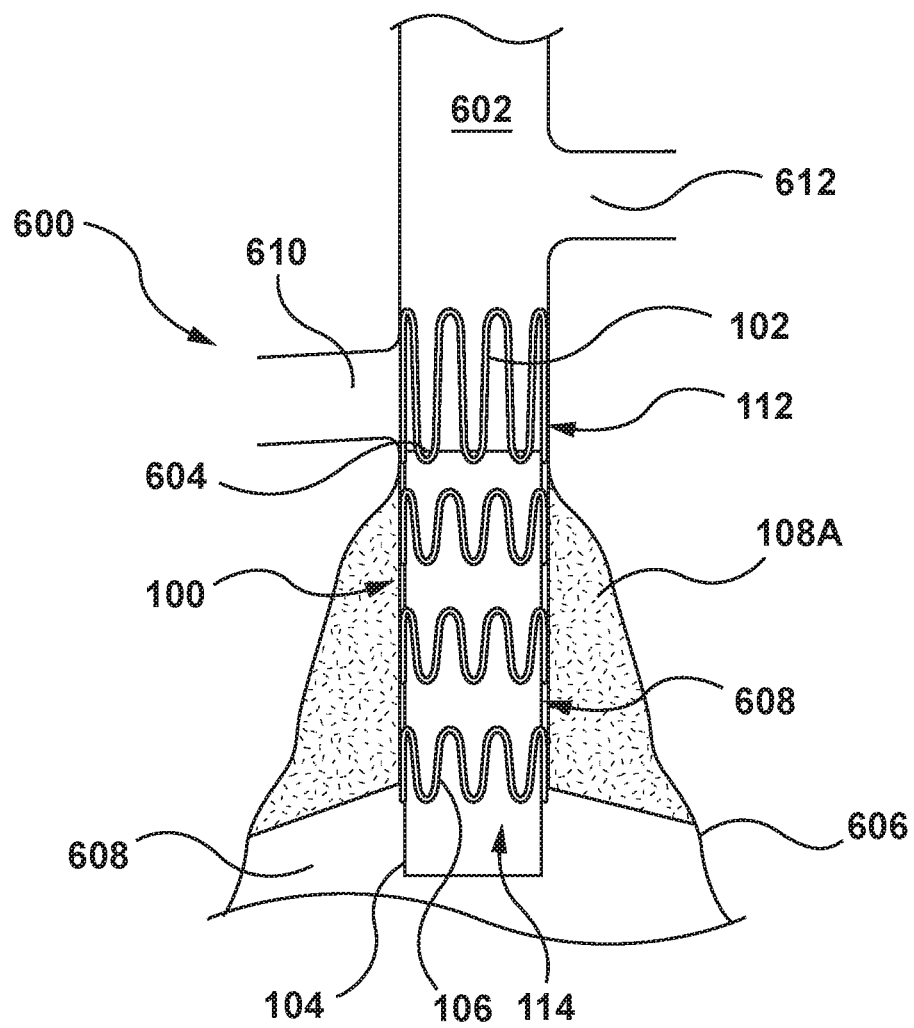
FIG. 6 shows a method of treatment using an endovascular prosthesis as described in embodiments herein.

In still further embodiments, methods of delivering a hydrogel-associated endovascular prosthesis 100 to a target blood vessel 602 of a patient are provided herein, and illustrated generally in FIG. 6. In suitable such embodiments, the methods comprise providing a hydrogel-associated endovascular prosthesis 100 having a compressed configuration for delivery within a vasculature and a radially-expanded configuration (shown in FIG. 6) for deployment within the target blood vessel 602.

As described throughout, suitably the endovascular prosthesis 100 for use in such methods comprises an anchor stent 102 for engaging an inner wall of the target blood vessel 602 when the prosthesis is in the radially-expanded configuration. The endovascular prosthesis further comprises tubular body 104 formed from a graft material 110 defining a central lumen 116 from a first end 112 to a second end 114 thereof, wherein the anchor stent 102 is attached to the first end 112 of the tubular body 104, the tubular body 104 having an inner surface 118 and an outer surface 120. Body stent 106 is suitably attached to the outer surface 120 of the tubular body 104 for maintaining the tubular body in the radially-expanded configuration. The endovascular prosthesis 100 further comprises a hydrogel composition 108 associated with about 20% to about 100% of the outer surface 120 of the tubular body 104. The hydrogel composition 108, as described throughout, suitably comprises a hydrogel polymer and one or more of a stabilizing polymer, a biologically active agent and a bioabsorbable polymer. The hydrogel composition 108 in a non-expanded state prior to introduction into the blood vessel, and is capable of expanding to an expanded state following introduction into the target blood vessel 602 of the patient.

Exemplary compositions for use in the hydrogel composition are described and detailed herein.

The methods further comprise introducing the hydrogel-associated endovascular prosthesis transluminally into a selected portion of the target blood vessel 602. During the introducing, the hydrogel composition is in the non-expanded state. Methods for introducing the hydrogel-associated endovascular prosthesis are known in the art, and suitably include the use of various catheter systems, often utilizing a stent-graft delivery catheter, or other similar structures.

The methods further comprise radially expanding the endovascular prosthesis 100 into contact with the target blood vessel 602 (see FIG. 6). Methods for carrying out the radial expansion are known in the art and suitably include the use of a balloon catheter, or removal of a covering or sheath to allow endovascular prosthesis 100 to self-expand, as described herein and known in the art.

The methods described herein further comprise expanding the hydrogel composition to the expanded state within the target blood vessel. As discussed throughout, expansion of the hydrogel composition from a non-expanded state to an expanded state occurs when the hydrogel polymer in the hydrogel composition is hydrated with water (e.g., blood). As shown in FIG. 6, expansion of the hydrogel composition expands the hydrogel radially around the tubular body 104, filling in empty volume that surrounds endovascular prosthesis 100.

The methods described herein for delivery of a hydrogel-associated endovascular prosthesis are suitably used to mediate a complication that arises during, after, or as the result of an endovascular treatment.

Thus, in embodiments, also provided herein are methods of mediating a complication during an endovascular treatment of a target blood vessel of a patient. The methods suitably comprise providing an endovascular prosthesis having a compressed configuration for delivery within a vasculature and a radially-expanded configuration for deployment within the target blood vessel.

As described throughout, the endovascular prosthesis 100 suitably comprises an anchor stent 102 for engaging an inner wall of the target blood vessel 602 when the prosthesis is in the radially-expanded configuration. The endovascular prosthesis suitably further comprises a tubular body 104 formed from a graft material 110 defining a central lumen 116 from a first end 112 to a second end 114 thereof, wherein the anchor stent 102 is attached to the first end 112 of the tubular body, the tubular body having an inner surface 118 and an outer surface 120. Further, a body stent 106 attached to the outer surface 120 of the tubular body 104 for maintaining the tubular body in the radially-expanded configuration is suitably provided. The endovascular prosthesis 100 also comprises a hydrogel composition 108 associated with about 20% to about 100% of the outer surface of the tubular body. As described herein, the hydrogel composition suitably comprises a hydrogel polymer and one or more of a stabilizing polymer, a biologically active agent and a bioabsorbable polymer. The hydrogel composition is suitably in a non-expanded state and capable of expanding to an expanded state following introduction into the target blood vessel of the patient.

The methods further comprise introducing the endovascular prosthesis transluminally into a selected portion of the target blood vessel 602, wherein the hydrogel composition is in the non-expanded state. The methods further comprise radially expanding the endovascular prosthesis into contact with the target blood vessel 602, and expanding the hydrogel composition to the expanded state within the target blood vessel, thereby mediating the complication.

Exemplary complications that can be mediated by utilizing the methods described herein include, for example, an endoleak, a stent graft migration or a sealing of the body lumen 602 in short neck aneurysms.

Endoleaks are characterized by persistent blood flow within an aneurysm sac following endovascular aneurysm repair. In successful endovascular aneurysm repair, an aortic stent-graft used suitably excludes the aneurysm from the circulation by providing a conduit for blood to bypass the sac, and continue to flow through the vessel 602, and to branch vessels 610 and 612.

There are several causes of endoleak and they are generally be classified into five types as follows (see, e.g., radiopaedia.org/articles/endoleak):

Type I: leak at graft attachment site, which can be proximal, distal, or iliac occlude;

Type II: aneurysm sac filling via branch vessel, which can impact a single vessel, or two vessels or more;

Type III: leak through a defect in a graft, which can include junctional separation of the modular components of a graft, as well as fractures or holes involving the graft;

Type IV: leak through graft fabric as a result of graft porosity; and

Type V: continued expansion of aneurysm sac without demonstrable leak on imaging (a.k.a. endotension).

Type I endoleaks occur as a result of an inadequate seal at the site of the graft attachment. It may occur at the proximal end, distal end or where the components overlap. Blood flow leaks alongside the graft into the aneurysm sac. They are often the result of unsuitable patient (aneurysm) selection or device selection, but can also occur if the graft migrates.

Type II endoleaks are the most common after an abdominal aortic repair. Retrograde flow through branch vessels continue to fill the aneurysm sac. The most common culprit vessels are lumbar arteries, inferior mesenteric artery or internal iliac artery. Embolization of the branch vessel is indicated if the aneurysm sac continues to expand in size.

Type III endoleaks are caused by mechanical failure of the stent-graft. There may be a fracture of the stent-graft, hole or defect on the graft fabric, or junctional separation of the modular components. Causes may relate to defective device material, extreme angulation of a segment predisposing to fracture, or improper overlap of the modular components during insertion.

Type IV endoleaks occur when blood leaks across the graft due to its porosity.

Type V "leak" (also referred to as endotension) is not a true leak but is defined as continued expansion of the aneurysm sac without evidence of a leak site. It is also referred to as endotension. It is believed to be due to pulsation of the graft wall with transmission of the pulse wave through the perigraft space (aneurysm sac) to the native aneurysm wall.

As shown illustratively in FIG. 6, introduction of endovascular prosthesis 100, radially expanding the endovascular prosthesis, and swelling or expanding (swelling and expanded are used interchangeably herein when referring to hydrogel composition 108) the hydrogel composition 108 suitably provides a sealing at a short neck region 604 of aneurysm 606, suitably preventing a type I endoleak. The methods described herein are particularly useful for treatment at a short conical neck 604 where endovascular prosthesis 100 may have difficulty providing an adequate seal as neck 604 is so close to branch artery 610. In neck region 604, expanded hydrogel composition 108A suitably acts to stabilize a seal in an otherwise hostile anatomy.

In addition, in the aneurysmal sac area 608, expanded hydrogel composition 108A suitably expands into the sac, impeding blood flow and resulting in stasis which will favor thrombus formation. Expansion of the hydrogel composition within the sac also suitably acts to compress luminal thrombus. In such embodiments, the methods described herein help to reduce type II endoleak by creating a positive pressure within the sac that results in remodeling of the luminal thrombus which can help obliterate branch vessels that are potential sources of type II endoleaks.

Expanded hydrogel composition 108A also suitably provides anchoring for endovascular prosthesis 100, suitably preventing movement of the prosthesis during any aneurysm sac remodeling over time. Such methods thus provide lower migration rates for the prosthesis and reduced complications.

The methods described herein are suitably used for treatment of mammalian patients, including for example, humans, dogs, cats, pigs, sheet, cows, etc. Suitably the patients are human patients.

In embodiments in which the hydrogel compositions comprise a bioabsorbable polymer or bioactive agent, use of such endovascular prostheses according the methods described herein suitably aids conversion of a thrombus in an aneurysmal sac into stable fibro-cellular tissue. Such conversion of a thrombus into fibrocellular tissue can also promote sac shrinking and elimination of a type II endoleak.

In embodiments in which a hydrogel polymer is mixed with a bioactive agent and/or bioabsorbable polymer, when the hydrogel composition 108 is expanded, the second material is suitably able to permeate into a thrombus, and hence more effectively, convert the thrombus into fibrocellular tissues.

As described herein, the hydrogel compositions can be associated (e.g., coated) on the entirety, i.e., over the entire length, of the outer surface of the tubular body, or on selected areas of the outer surface. For example, materials that enable conversion of a thrombus to fibrocellular tissue do not necessarily need to be applied where the endovascular prosthesis comes in contact with a neck of an aneurysm. Thus, in certain embodiments, the hydrogel composition can have different compositions over the length of the tubular body, depending on the ultimate application. For example, certain sections of the tubular body can be associated with a hydrogel composition containing a hydrogel polymer only, while another section can be associated with a hydrogel composition containing a hydrogel polymer and a biologically active agent and/or bioabsorbable polymer.

While the method steps described above are presented in a given order, alternative embodiments may perform steps in a different order.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of delivering a hydrogel-associated endovascular prosthesis to a target blood vessel of a patient, the method comprising:
    providing a hydrogel-associated endovascular prosthesis having a compressed configuration for delivery within a vasculature and a radially-expanded configuration for deployment within the target blood vessel, the prosthesis comprising:
        an anchor stent for engaging an inner wall of the target blood vessel when the prosthesis is in the radially-expanded configuration;
        a tubular body formed from a graft material defining a central lumen from a first end to a second end thereof, wherein the anchor stent is attached to the first end of the tubular body, the tubular body having an inner surface and an outer surface;
        one or more body stents attached to the outer surface of the tubular body for maintaining the tubular body in the radially-expanded configuration; and
        a hydrogel composition associated with only the outer surface of the graft material of the tubular body, wherein the hydrogel composition is in a non-expanded state and configured to swell to an expanded state following introduction into the target blood vessel of the patient and contact with blood;
    introducing the hydrogel-associated endovascular prosthesis transluminally into a selected portion of the target blood vessel, wherein the hydrogel composition is in the non-expanded state prior to the introducing;
    radially expanding the endovascular prosthesis into contact with the target blood vessel;
    contacting the hydrogel composition with blood; and
    swelling the hydrogel composition radially outward into the expanded state within the target blood vessel to fill in empty volume that surrounds the endovascular prosthesis.

2. The method of claim 1, wherein the swelling the hydrogel composition fills an aneurysmal sac or neck region of an aneurysmal sac.

3. The method of claim 1, wherein the swelling the hydrogel composition compresses tissue or other structures which surround the endovascular prosthesis.

4. The method of claim 1, wherein the swelling the hydrogel composition mediates an endoleak.

5. The method of claim 1, wherein the swelling the hydrogel composition prevents migration of the endovascular prosthesis.

6. The method of claim 1, wherein the swelling the hydrogel composition seals a short neck region of an aneurysm.

7. The method of claim 6, wherein the hydrogel composition is present only on the graft material that contacts the short neck region.

8. The method of claim 6, wherein the hydrogel composition is present on the graft material that contacts the short neck region and present on the graft material that contacts an aneurysm.

9. The method of claim 8, wherein the hydrogel composition present on the graft material that contacts the aneurysm further comprises a biologically active agent.

10. The method of claim 9, wherein the biologically active agent is a prothrombic material.

11. The method of claim 6, further comprising preventing a type I endoleak.

12. The method of claim 1, wherein the hydrogel composition is co-formed with the graft material as an integrated hydrogel composition-graft material structure.

13. The method of claim 1, wherein the hydrogel polymer is selected from the group consisting essentially of poly (hydroxyethyl methacrylate) (pHEMA), poly (vinylpyrrolidinone) (PVP), poly(acrylamide) (pAM), and poly(acrylic acid) (pAA).

14. The method of claim 1, wherein the stabilizing polymer is one of poly(ethylene terephthalate) and poly(urethane).

15. The method of claim 1, wherein the biologically active agent is selected from the group consisting essentially of collagen, fibrin, thrombin, and dipyridamole.

16. The method of claim 1, wherein the bioabsorbable polymer is selected from the group consisting essentially of poly(lactic-co-glycolic acid), poly(lactic acid) and poly (glycerol sebacate).

17. The method of claim 1, wherein the graft material is a flexible sheet of a material selected from the group consisting essentially of polytetrafluoroethylene (PTFE), expanded PTFE (ePTFE), ultra-high-molecular-weight polyethylene (UHMWPE), polyurethane and polyester.

18. The method of claim 1, wherein the hydrogel composition is covering about 20% to about 50% of the graft material of the outer surface of the tubular body.

19. The method of claim 1, wherein the hydrogel composition is covering about 50% to about 100% of the graft material of the outer surface of the tubular body.

20. The method of claim 1, wherein the hydrogel composition comprises a first hydrogel layer and a second biologically active agent layer.

21. The method of claim 20, wherein the second biologically active agent layer comprises a pro-thrombic material.

22. The method of claim 1, wherein the one or more body stents are completely free of the hydrogel composition.

* * * * *